United States Patent
Gugel et al.

(10) Patent No.: US 6,176,703 B1
(45) Date of Patent: Jan. 23, 2001

(54) MEDICAL OR DENTAL TREATMENT INSTRUMENT FOR CHIP-REMOVING TREATMENT OF BODY TISSUE OR A SUBSTITUTE MATERIAL WITH AN ABRASIVE TOOL

(75) Inventors: Bernd Gugel, Ulm; Gerd Löhn, Biberach-Rissegg; Walter Mössle, Mittelbiberach; Uli Xeller, Biberach, all of (DE)

(73) Assignee: Kaltenbach & Voigt GmbH & Co., Biberach (DE)

(*) Notice: Under 35 U.S.C. 154(b), the term of this patent shall be extended for 0 days.

(21) Appl. No.: 09/050,119

(22) Filed: Mar. 30, 1998

(30) Foreign Application Priority Data

| Apr. 18, 1997 | (DE) | 197 16 416 |
| Oct. 13, 1997 | (DE) | 197 45 245 |
| Nov. 21, 1997 | (DE) | 197 51 584 |

(51) Int. Cl.[7] ............................................. A61C 17/00
(52) U.S. Cl. ................................ 433/120; 433/118
(58) Field of Search ........................... 433/118, 120, 433/114, 119

(56) References Cited

U.S. PATENT DOCUMENTS

| 3,645,255 | * | 2/1972 | Robinson ............................ 433/119 |
| 4,427,384 | * | 1/1984 | Sertich ................................ 433/120 |
| 4,453,919 | * | 6/1984 | Takeshita ............................ 433/120 |
| 4,484,893 |   | 11/1984 | Finn ................................... 433/118 |
| 4,578,033 | * | 3/1986 | Mossle et al. ...................... 433/120 |
| 4,589,847 | * | 5/1986 | Loge et al. ......................... 433/126 |
| 5,190,456 | * | 3/1993 | Hasegawa .......................... 433/120 |
| 5,232,363 | * | 8/1993 | Meller ................................ 433/120 |
| 5,496,172 | * | 3/1996 | Albelda et al. ..................... 433/120 |

FOREIGN PATENT DOCUMENTS

| 379505 | 1/1986 | (AT) . |
| 2 132 434 | 11/1972 | (FR) . |
| 2 505 172 | 11/1982 | (FR) . |
| 2 550 439 | 11/1984 | (FR) . |
| 2 613 090 | 9/1988 | (FR) . |
| WO96/14024 | 5/1996 | (WO) . |

* cited by examiner

Primary Examiner—Ralph A. Lewis
(74) Attorney, Agent, or Firm—Fitzpatrick, Cella, Harper & Scinto

(57) ABSTRACT

In a medical or dental treatment instrument (1) for chip-removing treatment of body tissue or a substitute material with an abrasive tool (7), consisting of a handpiece (2) with an oblong gripping sleeve (41), in the front end area of which a vibration part (4) is supported, which can be set vibrating by a vibration generator (5), the handpiece (2) being connected or connectable at its rear end area to a flexible supply line (18), which extends from a supply device, the output of the vibration generator (5) is variable, and a control device (72) is provided with which the output can be increased or reduced.

29 Claims, 7 Drawing Sheets

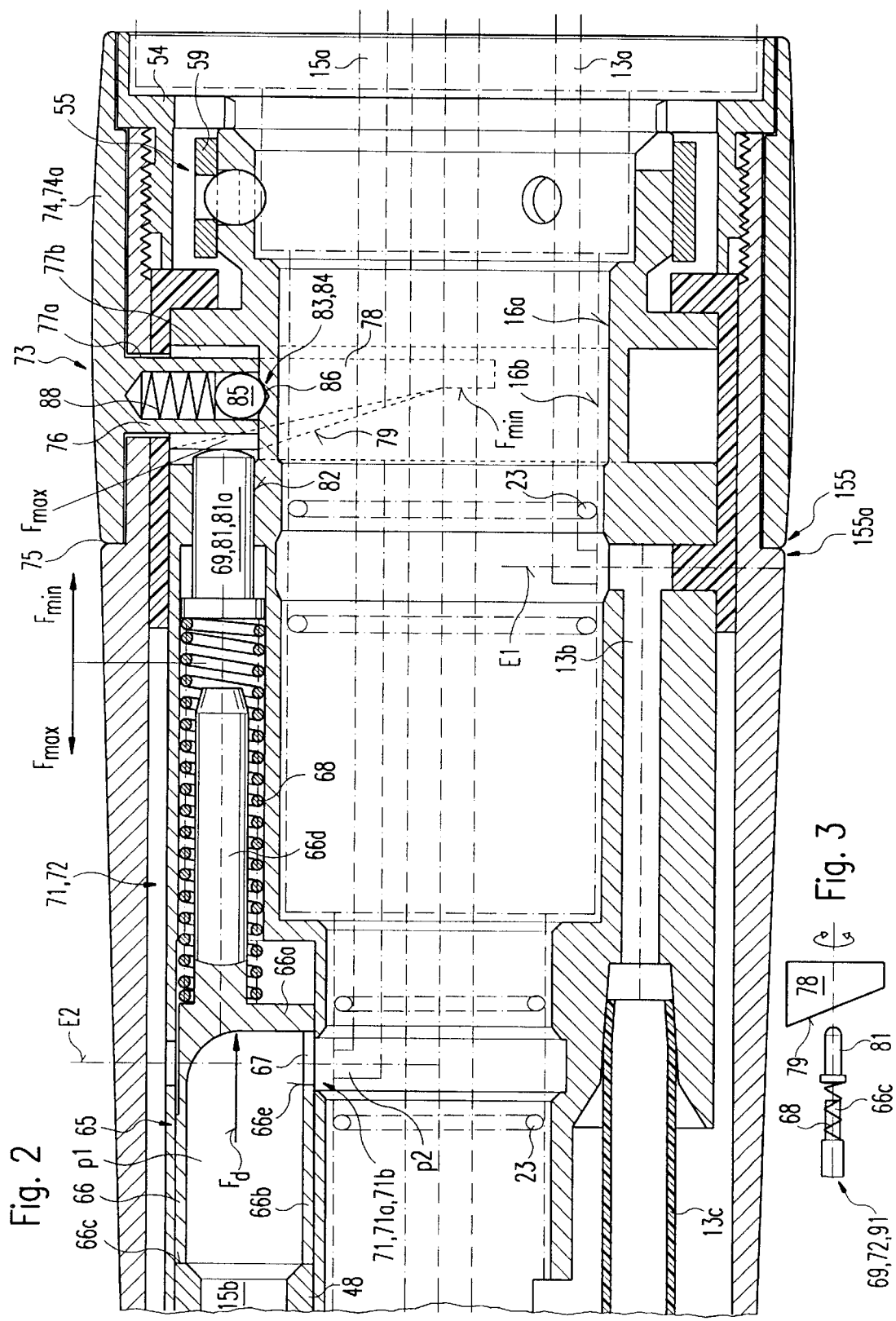

MEDICAL OR DENTAL TREATMENT INSTRUMENT FOR CHIP-REMOVING TREATMENT OF BODY TISSUE OR A SUBSTITUTE MATERIAL WITH AN ABRASIVE TOOL

BACKGROUND OF THE INVENTION

1. Field of the Invention

This invention relates to a medical or dental treatment instrument of the type which vibrates an abrasive tool for chip-removing treatment of living tissue.

2. Description of the Related Art

Treatment instruments with an abrasive tool and a vibration drive of a frequency lying preferably in the sonic or ultrasonic range are known for the chip-removing treatment of body tissue or a substitute material (tissue substitute or a prosthesis). A treatment instrument of this kind is described for example in WO 96/14024. It has an oblong handpiece in the form of a sleeve-shaped casing, in the front area of which a vibration part is supported in an elastically flexible manner, which part can be set vibrating in functional operation by a vibration generator and is connectable detachably in its front area to the tool by a holding device. In the rear end area, the handpiece has a coupling part, in particular a screw-on or plug-in coupling part, with which it can be coupled to a so-called connection piece of a supply device in the form of a flexible hose, which extends to a supply and control device and contains media lines for providing energy and supplying treatment media such as water, air or a spray.

A treatment instrument of this kind can be used in the dental field also as a device for removing tartar, a treatment instrument of this kind known from the Austrian patent specification 379 505 having a tool with a wedge-shaped working tip.

The known treatment instruments are coordinated with reference to their vibration function to a certain type of tool or to a certain treatment. The application range of such a treatment instrument is thereby restricted.

SUMMARY OF THE INVENTION

It is an object of this invention to improve a treatment instrument of the type described above in order to make it suited to a wide range of uses.

This object is achieved according to one aspect of the invention by providing a vibration part, a vibration generator and a control device, all arranged in a handpiece. The vibration part extends from the front end area of the handpiece and supports a tool. The vibration generator is connected to the vibration part for setting it into vibration. The vibration generator is variable and is connectable via a flexible supply line to a power supply; and the control device is arranged to increase and decrease the output of the vibrator.

According to a more specific aspect of the invention, a control device for increasing and reducing the output of a treatment instrument is assigned to the vibration generator, which facilitates the adjustment of an output setting in increments or steplessly. It is thereby possible to adapt the output of the treatment instrument to different treatments. The treatment instrument according to the invention is suitable for a wide range of uses, e.g. for treatments using different tools, in particular of varying size and/or shape and/or removal capacity (abrasiveness), with which it can optionally be fitted. In addition, both in cases where just one tool and different tools are available, the output of the treatment instrument is adaptable to treatments of differing intensity, to be precise rough and fine treatments or rough, medium and fine treatments, it being possible to effect these modifications taking identical materials or different materials, -of the tool and/or the material to be treated into account. The configuration according to the invention also facilitates adaptation of the treatment instrument to different types of treatment, e.g. for the removal of coatings, as in the case of a tartar removal device, or for working out a cavity, as in the case of preparing a tooth, for example.

A vibratory medical or dental treatment instrument of the present type can be susceptible to faults in respect of its power output, since the vibration generator which is contained therein is designed to emit a constant and defined vibration output, in order to achieve an optimum vibration operation. The optimum vibration operation can be impaired relatively easily when the output magnitude is changed. This often causes undesired vibration resonances which exert a detrimental effect on the vibration behavior. This is true in particular in case of a treatment instrument having a vibration generator which can be driven by compressed air.

Accordingly, it is another object of the invention to configure a treatment instrument of the above described type such that a constant vibration output is achieved irrespective of changes in supply pressure.

This object is achieved by providing a vibration part and a vibration generator arranged in a handpiece. The vibration part extends from the front end area of the handpiece and supports a tool. The vibration generator is connected to the vibration part for setting it into vibration. The vibration generator is drivable by compressed air from a flexible supply line which extends from the rear of the handpiece and which is connectable to a compressed air power supply. A pressure regulator is provided in the supply line and is constructed to provide an essentially constant working pressure at the vibration generator even in the presence of operating pressures of different levels.

According to a more specific aspect of the invention, a pressure regulator is provided in the treatment instrument in a manner which ensures that a constant working pressure is maintained at the vibration generator. It is thereby guaranteed that in the event of scarcely avoidable fluctuations in the operating pressure, or if the treatment instrument is used at treatment locations at which different operating pressures prevail (different manufacturers), the vibration output remains the same and thus an optimum vibration operation can be maintained.

It is particularly advantageous to provide an adjustable pressure regulator, so that setting the output magnitude and an optimum output setting is possible in each case independently of the operating pressure level.

In a treatment instrument of the type described above, a vibration generator in the instrument is driven pneumatically by compressed air. The compressed air flows through and produces vibrations is a vibration part by mechanical impact. In a vibration generator of this kind, noise is created which can be considerable and distract the user of the instrument.

It is therefore another object of the invention to reduce the drive noise in a treatment instrument of the above described type.

This object is achieved by providing a vibration part and a vibration generator arranged in a handpiece. The vibration part extends from the front end area of the handpiece and supports a tool. The vibration generator is connected to the vibration part for setting it into vibration. The vibration generator is connected to a flexible supply line which extends from the rear of the handpiece and which is connectable to a power supply. The vibration generator is surrounded by an additional inner casing.

According to a further aspect of the invention, the vibration part is encapsulated in an additional internal casing. The additional casing serves to deaden the drive noise so as not to disturb the user significantly. The configuration and arrangement of the additional internal casing according to the invention, is also distinguished by a simple, small construction which can be manufactured cheaply and assembled or dismantled easily.

It is also an object of the invention to provide an instrument of the above described type which can be used for treatment of teeth and which avoids or reduces damage to the teeth in the event of contact with the handpiece shank.

This object is achieved by providing a vibration part and a vibration generator arranged in a handpiece. The vibration part extends from the front end area of the handpiece and supports a tool. The vibration generator is connected to the vibration part for setting it into vibration. The vibration generator is connected to a flexible supply line which extends from the rear of the handpiece and is connectable to a power supply. The vibration part has a shank which protrudes from the handpiece; and a protective sheath of elastically flexible material is arranged on the shank.

According to a still further aspect of the invention, the handpiece shank of the instrument has a protective sheath of elastically flexible material, which avoids the aforementioned damage in a simple and inexpensive manner. The protective sheath can also serve to stabilize the elastic bearing of the vibration part in the front end area of the handpiece.

In a further configuration according to the invention an elastically flexible bearing for a vibration part is provided in the front end area of the handpiece and is substantially stabilized. In addition an elastically flexible and thus a gentle bearing is also provided for an optical fiber extending through the handpiece, which considerably reduces the risk of breakage.

Other aspects of the invention include features which contribute to provide a simple, small and functionally reliable construction which can be produced durably and cheaply, which can guarantee easily manoeuvrable operation and permit simple assembly or dismantling.

BRIEF DESCRIPTION OF THE DRAWINGS

FIG. 2 shows the detail indicated by X in FIG. 1 in an enlarged representation;

FIG. 3 shows the detail according to FIG. 2 in a simplified diagrammatic representation;

DETAILED DESCRIPTION OF THE PREFERRED EMBODIMENTS

Figure 1:
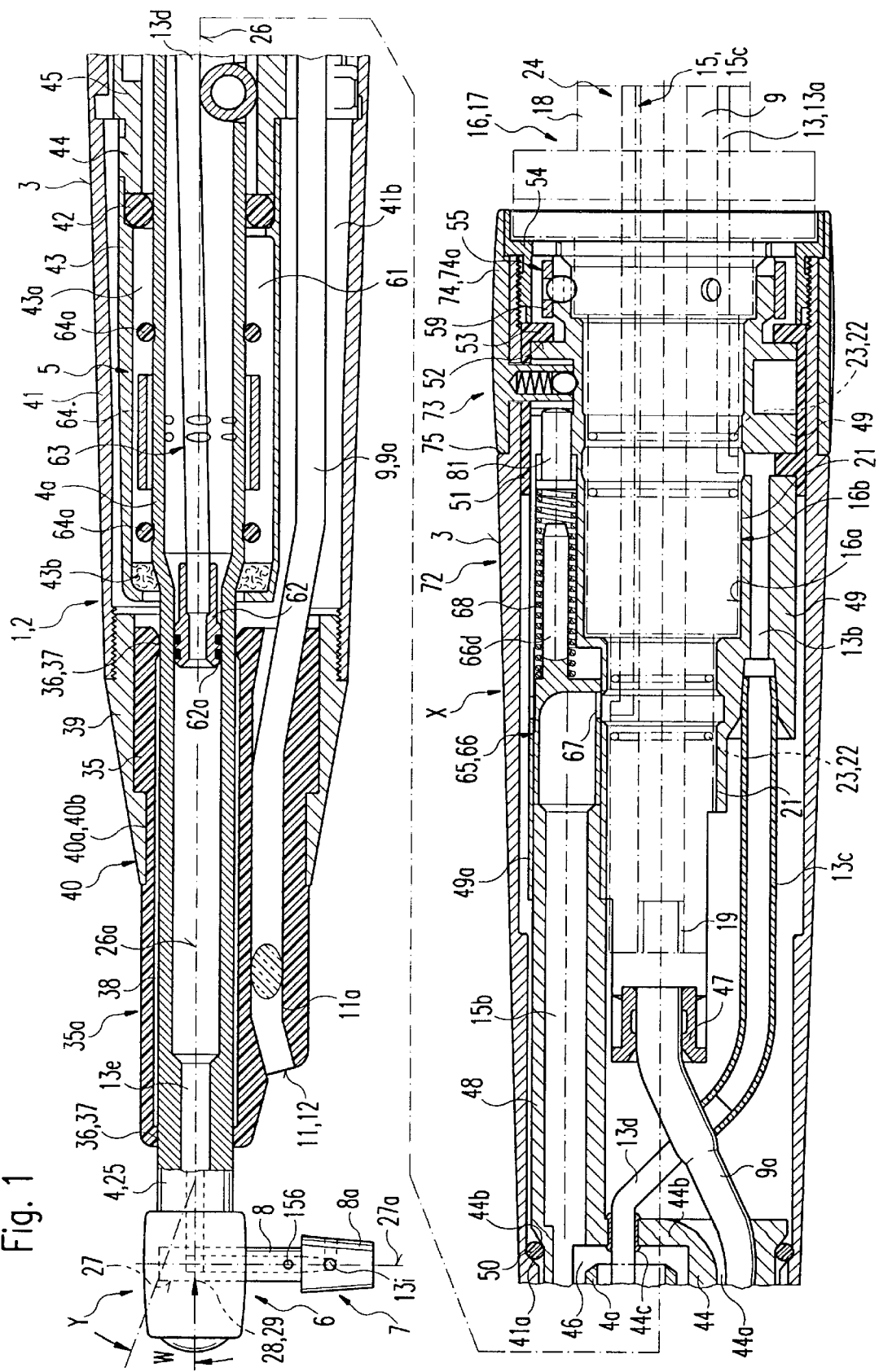
FIG. 1 shows a treatment instrument according to the invention for treating body tissue or a substitute material in axial section.

As shown in FIG. 1. a, treatment-instrument, comprises an oblong or rod-shaped handpiece 2. The handpiece includes a gripping sleeve 3, in which a preferably oblong or rod-shaped vibration part 4,4a is supported vibratably and can be set vibrating or driven by a vibration generator 5 which is also provided in the sleeve 3. A holding device 6 is attached to a forwardly protruding portion 4 of the vibrator part 4,4a. A treatment tool 7, has a tool shank 8, which is connectable detachably to the holding device 6.

It is advantageous to configure the treatment instrument 1 with at least one, preferably several, so-called media lines, which serve to supply drive energy and treatment media such as e.g. a treatment fluid and/or compressed air to the tool 7 and to supply light to the treatment point at which the tool operates. In the present configuration, a light guide 9 is provided, which extends lengthways through the handpiece 2 as far as its front end area and emerges at an exit opening 11 directed at the treatment point, thereby forming an illumination device 12. A line 13 is also provided extending lengthways through the handpiece 2 for delivery of a treatment or cooling fluid, here water, which line likewise emerges at an exit opening 14 (FIGS. 4 and 7) the front end area of the handpiece 2 and is directed at the treatment point, thereby forming a supply device.

A supply line 15 which supplies drive energy to the vibration generator 5, extends lengthways through the handpiece 2. The vibration generator 5 in this embodiment is driven by compressed air which is transmitted along the supply line 15 to the vibration generator 5.

The handpiece 2 is detachably connectable at the rear thereof to a connective piece 17 by a quick connector or a screw-on or plug-in connector such as a freely rotatable twist-on connector 16. The connection piece 17 is connected by a flexible supply line 18 to a remote supply and control device (not shown). The twist-on connector 16 is formed in the case of the present embodiment by a hollow cylindrical or stepped hollow cylindrical connection recess 16a within the gripping sleeve 3 of the handpiece. A cylindrical or stepped cylindrical connection pin 16b is insertable in the recess 16a so as to allow some movement or play. The connection recess 16a is disposed in the rear area of the handpiece 2 with the connection pin 16b projecting from the connection piece 17. The media lines extend through penetrate the twist-on connector 16; and are constructed such that in the event of separation of the handpiece 2 from the connection piece 17, the media lines are automatically interrupted. The light guide 9 extends through and along the axis of the twist-on connector 16. A rear light guide section extends coaxially from a corresponding receiving hole, in the connector 16 and up to the front end area of the connection pin 16b. A front light guide section is connected at a plane of separation between the connector 16 and the connection piece 17 and which extends through the connector 16 as far as an exit opening 14. The front light guide section is preferably formed by an optical fiber 9a of light-conducting material, such as for example glass or synthetic material, a flexible optical fiber or a rigid optical fiber preferably in the form of a molded body. The cross-sectional shape of the optical fiber 9 is preferably round at its rear and is elliptical further forward. The rear light guide section can likewise be formed by an optical fiber (not shown) or by an electrical line with a lamp 19 disposed in the front end area of the connection pin 16b, which lamp may be arranged in a recess open at the front of the connection pin.

The two other media lines 13, 15 extend through a hollow cylindrically shaped plane of separation 21 between the connection pin 16b and the wall of the connection recess 16a in the handpiece 2. As shown, the lines 13 and 15 are bent in a Z-shape so that the pins are in radial directions through the cylindrical plan 21. The lines 13 and 15 extend through respective openings, in a corresponding sheath surface of the connection pin 16a and the inner sheath surface of the connection recess 16b, in the handpiece 2. The lines 13 and 15 lie in an annular groove 22 in the sheath surface or in the inner sheath surface. This arrangement guarantees media passage in each rotary position of the twist-on connector 16 even beyond 360°. The regions where the radial lines 13 and 15 extend through the cylindrical plane 21 are each sealed by a sealing ring 23, in particular an O-ring, which is arranged on both sides of the Z-shaped penetration point in an annular groove in the sheath surface of the connection pin 16b or the inner 5 sheath surface of the connection recess 16a. Connections, e.g. connecting sleeves 24 for media line sections running in the flexible supply line 18 can be arranged at the rear on the connection piece 17.

The holding device 6 for the tool 7 is disposed in the front end area of the vibration part 4. In the present configuration the vibration part 4 is a rod- or sleeve-shaped body, which is arranged in, the front half of the handpiece 2 and forms a handpiece shank 25, which projects from the front end of the handpiece 2 and can extend straight or can enclose an acute angle W of approximately 10 to 30°, in particular approximately 20°, with reference to the longitudinal center axis 26 of the handpiece 2. The holding device 6 has a plug-in hole 27 extending transversely or preferably at right angles to the handpiece shank 25, which hole is preferably a blind hole and is thus only open on one side, and into which the tool shank 8 is pluggable with slight movement play. To secure the tool 7 in the plugged-in position, a securing recess 28 is provided in the tool shank 8. A securing part 29 is movable in the recess 28 and is adjustable in the longitudinal direction of the handpiece shank 25. The securing part is adjustable between a securing position, where it has moved into the securing recess 28, and a release position where it has moved out of the recess to release the tool shank 8. The securing part is preferably acted upon by the force of a spring to move it into its securing position. The securing recess 28 can be an annular groove. Several spherical caps disposed uniformly distributed on the circumference of the groove can also be provided. These caps can have preferably wedge-shaped hollows with a central core free hole.

The handpiece shank 25 extends as a vibrating rod 4a in the area of the handpiece 2; and it is supported against elastic restoring forces in a radially and preferably also axially flexible or movable manner in the handpiece 2. This is achieved by a bearing sleeve 35 of elastic material, e.g. synthetic material or rubber, in the front end area of the handpiece 2. The vibrating rod 4a is taken up with circumferential contact, so that it is centered by the bearing sleeve 35. In the present configuration, the bearing sleeve 35 has, in its front and rear end area, radially inwardly projecting bearing beads 37, which are preferably rounded in cross-section. An annular gap 38 is formed between the vibrating rod 4a and the bearing sleeve 35. The bearing sleeve 35 can be fixedly disposed in a sleeve cover 39, which itself is fixedly connected to a sleeve casing 41, e.g. screwed into it, as shown in FIG. 1. The sleeve casing 41 terminates steplessly with the cover 39 to form the gripping sleeve 3.

The bearing sleeve 35 extends beyond the sleeve casing 41 and the sleeve cover 39 and thus forms a protective sheath 35a for the handpiece shank 25. The shank 25 extends beyond the bearing sleeve 35 to the holding device 6 or an actuating element yet to be described. In order to fix the bearing sleeve 35 and/or the protective sheath 35a, a formfit connection 40 is provided with an annular groove 40a and an annular neck 40b bordering therein. The groove 40a engages automatically on insertion owing to the elastically deformable of the bearing sleeve 35. Due to the protruding elastic or soft elastic protective sheath 35a, damage resulting from the vibration on contact of the tool shank with adjacent body parts, e.g. teeth, during treatment is avoided. It is also possible to arrange the protective sheath so that it is fixed as a separate component only on the tool shank 25, e.g. pushed onto it in an elastically squeezing manner or fixed thereon by means of a corresponding form-fit connection 40.

A rear area 4a of the vibrating rod 4 is supported by a radially and axially elastically flexible support which is formed by a bearing ring 42 of elastically deformable material such as synthetic material or rubber. The ring 42 may be an O-ring which contacts the exterior of the rear area 4a of the vibrating rod 4a sits with external contact, the bearing ring 42 is taken up and supported in a sleeve 43 which surrounds the rear end portion 4a of the vibrating rod 4 and defines with the rod, a radial annular space 43a. Alternatively the reception of the sleeve 43 may be supported in a bearing section 44 extending rearwardly from the sleeve. In this case, the sleeve or bearing section 43 is supported in the sleeve casing 41 such that it is radially and axially immovable or preferably is movable against a restoring force. The sleeve is inserted from behind and sits with a front locating face closely to a rear locating face of the sleeve casing 41. The bearing section 44 is cylindrical and has a front sleeve projection 45 which surrounds the rear portion 4a of the vibrating rod 4 at a radial distance, with the rear end portion 4a of the vibrating rod 4 ending in a free space 46 of the bearing section 44. The front sleeve projection 45 of the bearing section 44 is connected in a mutually overlapping arrangement with the sleeve 43 and is preferably pushed on or in closingly and sealed by a seal, which is formed here by the bearing ring 42.

The rear end portion 4a of vibrating rod 4 is arranged with its associated bearing elements being coaxial to the longitudinal center axis 26. In the present configuration, the longitudinal center axis 26a of the vibrating rod 4 is offset with reference to the longitudinal center axis of the front end region of the gripping sleeve 3 and the bearing sleeve 35. This eccentric arrangement permits the exit opening 11 and related through-duct 11a, through which the optical fiber 9a extends, to be directed at the tool 7. The rear end of the optical fiber 9a is secured by a bearing sleeve 47 which is located in an extension of the connection recess 16a. The optical fiber 9a extends forwardly through an eccentric or off-axis through-duct 44a in the bearing section 44. Also arranged in an off-axis position opposite the optical fiber 9a in the bearing section 44 is an eccentric rear pipe socket 48. A sleeve projection 49a of a connecting sleeve 49, is connected to the rear of the pipe socket 48. The sleeve projection 49a may be either supported alone or with the bearing section 44 as an assembled component held radially on all sides and movable axially against a restoring force in the sleeve casing 41. This support is achieved by means of a bearing ring 51 of elastically deformable material which surrounds the connecting sleeve 49. The bearing ring 51 centers the connecting sleeve 49 owing to the ring's elastic restoring force. Thus, the ring 51 supports the sleeve 49 radially in an elastically flexible manner. The bearing ring 51 preferably has an inner flange 53 engaging behind a rear locating face 52, which flange also supports the connecting sleeve 49 in an elastically flexible manner in opposition to rearwardly directed axial forces. In the present configuration, the unit formed by the connecting sleeve 49 and the bearing section 44 is supported in an elastically flexible manner in both axial directions between the inner flange 53 and the bearing ring 42. In addition, an axially, and preferably also diametrically, effective bearing ring 50 of elastically flexible material can be disposed between related locating faces 41a, 44b, here between an inner shoulder of the sleeve casing 41 and an outer shoulder of the bearing section 44. With this arrangement, radial center and proper positioning is ensured owing to the elastic restoring force of the elastically flexible bearing elements. The bearing ring 51 is fixed positively in the axial direction due to the fact that an inner flange 53 thereof sits close to a forwardly facing surface of a threaded sleeve 54 which is screwed into the rear end of the sleeve casing 41.

As shown in FIG. 2 a manually pressurizable locking device 55 for pressurizable locking in the connection end position is provided in the rear area of the twist-on connector 16. In the illustrated arrangement, the locking device 55 has one or more locking elements, such as bolts, which are arranged along its circumference and which are positioned in radial holes of the connecting sleeve 49. The locking elements can dip into the holes by an amount such that they can engage in an annular groove in the connection pin 16b. on manual pressurization of the twist-on connector, the locking elements are pressed out of the annular groove automatically against an inwardly radially spring in the form of a split washer 59. The holes are tapered near their openings so that the locking element or elements cannot fall out when the connection pin-16b is removed.

Media lines 13 and 15, which supply compressed air from an external supply compressed air from an external supply, extend in the connection piece 17 as e.g. axially parallel ducts 13a, 15a. These ducts extend through the connection pin 16b and the connecting sleeve 49 to angled radially extending portions at axially separated transverse planes E1 and E2. The one through-transverse plane E1 is displaced axially with reference to the other through-transverse plane E2 of the compressed air line and the angular ducts angled portions of these ducts in the connecting sleeve 49 are designated respectively as 13b and 15b. A pipe or hose 13c is connected to the angular duct 13b of the line 13 for supplying treatment fluid. The pipe or hose 13c is connected downstream to a further pipe or hose 13d, which extends through a rear wall 44b of the bearing section 44 in a sealed manner in a bushing sleeve 44c and extends in the cavity 61 of the rear end portion 4a of the sleeve-shaped vibrating rod 4 as far as its middle area. An end sleeve 62 sits sealed by means of one or two sealing rings 62a in the rear end portion 4a of the sleeve-shaped vibrating rod 4 and is connected tightly to a pipe 13d.

A control device 72 is provided for the vibration generator 5 for reducing or increasing its output. In this manner the capacity or the amplitudes and intensity of its vibrations of the generator, that is, oscillations and the magnitude of the amplitudes are thereby made adjustable. In this regard an output regulator 71 described in detail herein below can be provided in order to provide automatic regulation either to maintain a constant output or to provide manually adjustable control. The control device 72 can be provided, with a regulator to vary the output or the amount of drive energy which is supplied to the vibration generator 5 such that the amount of energy is variable and can be reduced and increased and automatically. Also a manual setting device 73 may be provided, to achieve manual adjustments in increments or steplessly. The output of the treatment instrument can thereby be adapted to the work to be performed, e.g. rough and fine work, rough, medium and fine work or to different types of treatment tools 7 which may be different in shape, size and/or abrasiveness.

The manual setting device 73 has a setting element 74, which is manually accessible from outside and which is adjustable axially or in a circumferential direction. The device 73 is in drive connection with the control device 72. In the illustrated configuration, the setting element 74 is in the form of a sleeve 74a, which surrounds the handpiece 2, preferably in its rear area. The sleeve 74a is sunk in an annular recess 75, which forms an annular guide. Thus the sleeve is adjustable axially or preferably in a circumferential direction. In the illustrated configuration, the annular recess 75 is limited at the rear by a locating face of the screw-in sleeve 54. Protruding radially inwards from the inner sheath surface of the setting sleeve 74a is a bearing web 76, which extends over a part of the circumference of the sleeve and which extends through and slots 77a, 77b in the sleeve casing 41 and in the components arranged inside the casing. The web 76 is allowed some movement or play. A segment 78 extends over a section of the circumference of the sleeve, and has an oblique or curved face 79 on one side, which interacts with an adjusting element 81 which in turn is in effective contact with the control device 72, as shown diagrammatically in FIG. 3 and as in an actual construction in FIGS. 1 and 2. The oblique or curved face 79 can be disposed at the front and the rear of the segment 78. In the illustrated configuration the setting element 74 is located in the rear end area of the handpiece 2 the oblique or curved face 79 is disposed at the front. In this case the adjusting element 81 is an adjusting pin 81a and is supported in a guide pin 82 so that it may be displaced parallel to the longitudinal axis of the handpiece. The pin 81a is acted upon by the force of a spring, such as a pressure spring, against the oblique or curved face 79 and is thus moved axially when the adjusting element 74 is twisted back and forth. The guide 82 can be formed by a hole parallel to the longitudinal axis in the connecting sleeve 49, so that it is supported in a rotationally secured manner.

The setting device 73 can be set in increments or steplessly. In both cases it is advantageous to provide a fixing device 83 for the setting device 73. The fixing device facilitates fixing of the setting device 73 in each set position and thereby prevents unintentional adjustment. A braking device may be used here, which owing to its stiffness prevents accidental adjustment of the adjusting element 74. In the illustrated configuration, a pressurizable locking device 84 is provided with a locking element 85 which preferably formed by a ball and is guided for radial movement in a hole in the bearing web 76. The locking element 85 can be locked and unlocked manually by turning the setting sleeve 74a relative to spherical caps 86, which are arranged along an outer sheath surface of the connecting sleeve 49 in the base of the groove or slot 77b. The locking element 85 is supported to be radially displaceable in the radial hole in the bearing web 76. The locking element 85 is pre-tensioned against spherical caps 86 by a pressure spring 88 arranged in the radial hole. The adjusting element 81 acts on the vibration generator 5, which is adjustable so that its output can be increased or reduced with adjustment of the setting element 74.

In the illustrated example the vibration generator 5 is pneumatically drivable. In this regard the control device 72 has a control valve 65 for controlling the effective pressure p1 at the vibration generator 5. The setting element 74 is connected indirectly or directly to a valve slide 66, which in turn controls the size of a valve opening 67 depending on the setting of the setting element 74. The valve opening 67 is located in the supply line 15, which may be downstream of the connection pin 16b in the area of angular duct 15b. To reduce the vibration output, the slide valve 66 with the setting device 73 is displaced in the direction of reducing the valve opening 67. In the illustrated practical example displacement is in a forward direction, so that the valve opening 67 reduces the pressure p1 available at the vibration generator 5 in the sense of an adjustable choke. To increase the output, the valve opening 67 is increased in the reverse direction, whereby a greater available pressure p1 is set. The return of the setting element 74 can be effected by a recuperating spring, which pre-tensions the setting element 74 against the oblique or curved face 79.

In addition to or instead of the control device 72 for setting the available pressure p1, it is advantageous to provide an automatic pressure regulating device 71a with a pressure regulating valve 71b, which device or valve sets an essentially constant effective pressure p1 independently of the existing operating pressure p2 in the supply line section 15a. Essentially identical working conditions and an approximately comparable output or intensity of the tool 7 are hereby achieved on connection of the treatment instrument to supply lines 18 and supply devices with different operating pressures p2, in particular of different manufacturers, even in the event of considerable tolerances of the effective pressure p1.

Both in the case of the control valve 65 and a regulating valved 71b, the valve slide 66 is arranged in the supply line 15, here in the section of the supply line 15b parallel to the axis. The valve slide is preferably supported so that it is longitudinally displaceable in the valve 66. As can be seen, the valve opening 67 is controlled by an end face of the valve slide 66. The valve slide 66 can also have a pot-shaped form, and the valve opening 67 in the circumferential wall can be arranged in a pot shape.

In the illustrated example according to FIGS. 1 to 3, a control device 72 or a manual setting device 73 is provided in combination with a pressure regulating valve 71b. The valve slide 66 is acted upon on its one face by the effective pressure p1; and pre-tensioned the slide 66 may in opposition to this pressure toward its open position by means of a pressure spring 68 acting on its face. In the illustrated configuration, the valve slide 66 has the form of a round or out-of-round pot-shaped sleeve with a bottom wall 66a at its end opposite the vibration generator 5. The valve opening 67 is disposed in the radially internal circumferential wall 66b so that it interacts with the radial section of the supply line section 15b. In the open position, the valve slide 66 is forced by the spring 68 against a limit stop 66c, here the pipe socket 48. A spring mandrel 66d extends rearwardly from the slide valve 66 and a pressure spring 68 which sits on the mandrel is supported against a rear abutment 69, in this case the adjusting element 81.

In operation of the above described device, compressed air flows from the supply line section 15b through the annular gap at the rear of the handpiece and into the cavity 61 of the sleeve-shaped vibrating rod 4. The rear end 4a of the vibrating rod 4 has, in its middle area and ahead of the end sleeve 62, one or more radial and/or secantial flow-holes 63. The region of the rear portion 4a of the vibrating rod 4 is surrounded by a wobble sleeve or a vibration sleeve 64 with radial movement play. The sleeve 64 is disposed with axial movement play between two limit stops 64a, which can each be formed by a ring of elastic material, e.g. an O-ring, which sits in an annular groove in the rear end portion 4a of the vibrating rod 4. During the flow of compressed air through the gap between the rear end portion 4a of the vibrating rod 4 and the vibration sleeve 64, the latter is set into vibration, which it transmits by mechanical impact onto the vibrating rod. The gap is dimensioned such that the vibration sleeve 64 does not strike against the inner wall of the sleeve 43 surrounding it. Exhaust air flows out of the annular space 43a through an air-permeable bearing ring 43b which is arranged between the rear end portion 4a of the vibrating rod 4 and the front end area of the sleeve 43. The ring 43b can be perforated and can comprise an elastic or flexible material such as synthetic material or an air-permeable material such as e.g. felt. The exhaust air passes into the free cavity 41b of the sleeve casing 41 and through a suitable opening (not shown) which is preferably in the rear of the sleeve casing 41, and from there exits into the open air. Alternatively, the exhaust air may pass the duct 44a and exit through a suitable removal duct in the connection pin 16b into the open air. The bearing ring 43b is fixed axially, here between an if applicable wedge-shaped locating face on the rear end portion 4a of the vibrating rod 4 and an inner flange of the sleeve 43.

The sleeve 43 forms, in combination with the bearing ring 43b, an inner casing or encapsulation of the vibration generator 5, due to which significant noise reduction is achieved in a simple and cheap manner.

The valve opening 67 is an adjustable choke, which produces a pressure drop, which in turn defines the effective pressure p1. If the operating pressure p2 becomes greater or smaller than a defined value, the pressure p1 which generates force Fd urging the valve slide 66 against the spring 68 also changes. The position of the aperture edge 66e which defines the size of the valve opening 67 and thus also the magnitude of the choke, which generates the effective pressure p1, is determined by the balance of the spring force and the pressure force Fd. During operation, the valve slide 66 occupies a position remote from its limit stop or non-functioning position as shown, in which e.g. at an intermediate operating pressure p2, the valve opening 67 is set at a medium range size. At a lower operating pressure p2, the valve slide 66 is displaced into an equilibrium position (here to the left) in which it controls a larger valve opening 67. If the valve operating pressure p2 is increased, the valve slide 66 moves to an equilibrium position (here displaced to the right) in which it produces a smaller valve opening 67. Due to this function, the control valve 71b regulates a basically constant available pressure p1 automatically in the event of different operating pressures in a definable pressure range. This pressure regulation functions both in the absence of a control or setting device as well as in the case where the pressure or output regulator 71 is arranged in combination with the setting device, or even in the case where a manual setting control device acts on the pressure regulating valve 71b or on its valve slide 66. A common valve opening 67 preferably exists for the pressure regulating valve 71b and the manual setting device 73 or another control device 72. The cost of construction and manufacturing are thereby reduced considerably and the construction of the device is simplified.

In the illustrated example, the pre-tensioning force of the valve spring 68 is changed by means of the setting device 73. Specifically, this force is increased in the case of a requirement for a high output and it is reduced for the case of a requirement for a lower output. In the event of a higher output requirement, the adjusting element 81 is thus displaced in the direction of the control or regulating valve 65, 71b and for a lower output requirement the element 81 is displaced away from the control or regulating valve 65, 71b, for example backwards, as indicated by the reference symbols Fmin and Fmax. In the illustrated example, the output of the output regulator 71 is changed by means of the setting device 73 in the direction of an increase or decrease in the output deliverable at the tool 7. Specifically, this change is made independently of the magnitude of the operating pressure p2. In the case of a possible configuration within the scope of the invention and in the absence of the regulating valve 71b, the output can likewise be optionally reduced and increased by means of the manual setting device 73 or another control device 75. That is depending on the existing operating pressure p2, the adjusting element 81, which likewise acts on valve slide 66 of the control valve 65, now executes a control function. For this purpose the adjusting element 81 can be connected directly to the slide valve 66, for example by a spring mandrel 66d of a necessary length.

The treatment instrument 1 can hereby be adapted not only to different treatment methods but also to tools 7 of different shape and/or size and/or abrasive removal capacity, e.g. rough and fine or rough, medium and fine. It is also possible to adapt the treatment instrument taking account tools 7 of differing masses and/or shapes. Vibration states which are mutually disruptive due to a change in the vibration amplitudes can also be largely eliminated with the setting device 73 according to the invention.

The main direction of the vibrations of the vibration part 4 is essentially at right angles to its longitudinal axis and thus the vibrations are basically directed in the longitudinal direction of the tool 7. However, because of the radial and axial elastically flexible support of the vibration part 4, other vibrations appear which are caused spatially by resonances other conditions. As a result the tool 7 is also driven so that it is abrasively effective in a direction transverse thereto.

In the illustrated example, the oscillation or vibration drive has a frequency in the sonic or ultrasonic range from roughly 4 to 8 kHz, preferably roughly 6 kHz, an amplitude of spatial movement of roughly 0.05 mm to 0.2 mm, in particular approx. 0.1 mm.

The treatment instrument according to the invention is therefore particularly well suited to different tools 7, which are assigned to the treatment instrument as a tool range and differ from one another on account of their differing shape and/or size and/or purpose.

The holding device 6 according to the invention facilitates not only secure mounting of the tool 7 on the handpiece shank 25, but also simple, easy to handle and quick gripping and release of the tool 7. To release and remove the securing part 29 from the securing recess 28, an actuating element 91 (FIG. 4) is supported as a component which cannot be lost in the front end area of the handpiece shank and is movable in a guide between a ready position and a release position. The actuating element 91 is directly or indirectly in contact with the securing part 29; and its direction of movement between the ready or tool holding position and the release position runs parallel to the direction of movement of the securing part 29, namely, radial with reference to the tool shank 8. In the example illustrated in FIG. 4, the actuating element is an actuating slide 92, which is manually accessible laterally and/or from the side of the handpiece shank 25 opposite the tool 7 and is preferably formed by an actuating sleeve of synthetic material or preferably metal surrounding the hand, shank 25 and displaceable on it in its longitudinal direction. The hollow cylindrical sheath surface of the handpiece shank 25 forms a longitudinal guide 93 for the actuating slide 92. According to FIG. 4, the actuating sleeve 92a is designed to be so long that it projects beyond the plug-in hole 27 on both sides, having a plug-in recess 94 in alignment with the plug-in hole 27 on its side facing the tool 7. The recess 94 is formed, taking account of the adjusting path of the actuating sleeve 92a, by an oblong hole, which can extend out towards the rear of the actuating sleeve 92a in the form of a slot. The actuating sleeve 92a has a through-hole 95 which is offset forwardly with reference to the plug in recess 94 and with reference to the longitudinal center axis 27a of the plug-in through-hole 27 in the handpiece shank 25. A transverse pin 96 is supported in the through-hole 95, preferably with caps 97 placed on its ends. The transverse pin 96 or the caps 97 engage a slot 98 which preferably extends forwardly in the front end area of the handpiece shank 25 so as to allow some movement or play. The actuating sleeve 92a is hereby rotationally secured. The securing part 29 sits on the central area of the pin 96 and is formed with a corresponding transverse hole 99. The hole 99 in the illustrated example is formed with steps for the caps 97. The securing part 29 is located in a coaxial receiving hole 101 which extends forwardly in the handpiece shank 25 and is threaded in its front area. A securing lug 29a, in the form of a rounded dome, is provided at the rear of the securing part 29. The lug 29a has flanks which can be so steep that pressurizing of the locking device 102 thus formed by axial pulling on the tool 7 is not possible, or can progress so gradually that automatic displacement of the securing lug 29a from the securing recess 28 is possible only by pulling on the tool 7. A spring plate 103 in the shape of an annular bead is formed at the front of the securing part 29. A pressure spring 104 is disposed between the spring plate 103 and a spring plate 105 on a screwed lid 106 which in turn is screwed into the receiving hole 101. The screwed lid 106 can be covered at the front by a preferably convexly rounded cap 107, preferably of synthetic material. The cap 107 is locked by a locking pin 109 engaged in a locking hole 108 on the screwed lid 106. The latter has a tool engaging element for screwing and unscrewing. For this purpose two blind holes 111 extend into the lid 106 parallel to its axis. A tool with corresponding carrier pins is insertable into these blind holes. To seal the longitudinal guide 93, sealing rings 112, preferably in the form of O-rings, are provided at both sides of the plug-in hole 27. These sealing rings are arranged in annular grooves located in the outer sheath surface of the handpiece shank 25 or in the inner sheath surface of the actuating sleeve 92*a*. The rear base area of the slots 98 forms a limit stop 98*a* to limit backward movement of the securing part 29 in which the securing lug 29*a* projects into the plug-in hole 27. The locking device 102 thus far described for the tool shank 8 is functional and advantageous for reasons of advantageous and simple handling and secure mounting. On insertion of the tool shank 8 into the plug-in hole 27, the locking or securing lug 29*a* is displaced into its release positions by an insertion bevel 113 or curve is preferably also present on the free end of the tool shank 8 into its release position. Thus the tool shank 8 can be pushed further in until its free end meets the inner wall of the actuating sleeve 92*a*. In this position the securing lug 29*a* springs automatically into the related securing recess 28. The faces of the securing recess 28 preferably form a limit stop to limit movement to the securing position.

In the case where the securing recess 28 is formed by an annular groove, a mounting is provided for the tool shank 8 such that unbraked or free turning of the tool in the holding device 6 is possible. This free rotatability is guaranteed when the limit stop 98*a* is arranged so that the securing lug 29*a* indeed engages in the annular groove, but does not press against the base of the annular groove or only presses lightly against it.

Figure 4:
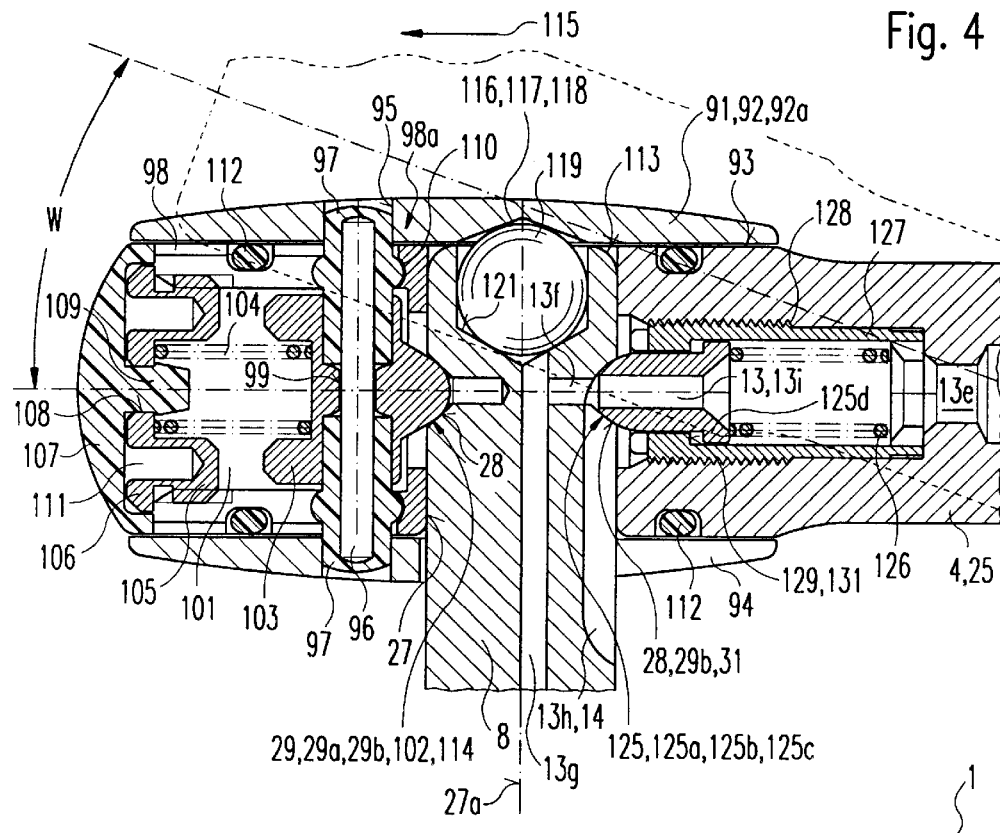
FIG. 4 shows the detail indicated by Y in FIG. 1, namely a holding device for a tool arranged in the front end area of the treatment instrument in axial section.

In the present configuration illustrated in FIG. 4, several spherical recesses 31 may be arranged circumferentially to form a rotary position setting device 114. This facilitates different rotary positions of the tool 7 due to the fact that locking in the related spherical recess 31 in each case forms a rotational securing.

It is possible here to develop the rotary position setting device 114 such that if a certain torque is exceeded, the locking device 110 is automatically pressurized and the securing lug 29*a* automatically forced out of the related spherical cap 31. With this arrangement the amount of torque needed to release the locking device 110 can be set by forming the conical surfaces of the spherical secures 31 at a certain angle.

To release the locking device 102 voluntarily, e.g. when a tool 7 is to be released or exchanged, the actuating element 91 is manually displaced in a forward direction by finger pressure in the direction of an arrow 115 against the force of the spring 104. This releases the locking device 102 and allows the tool shank 8 to be removed from the holding device 6.

In the case of a previously described locking device, an axial continuation of the line 13 as a duct 13*e* (FIG. 1) in the handpiece shank 25 as far as the plug-in hole 27 and radial and axial duct sections 13*f* and 13*g* in the tool shank 8 (FIG. 4) facilitates the supply of treatment fluid to the treatment point. The fluid is directed to emerge from exit openings (not shown) in the area of the abrasive working surfaces of the tool 7. Alternatively or in addition, a longitudinal groove 13*h* extending from the transverse area of the securing recess 28 to the tool body 8*a* can be provided in the sheath surface of the tool shank 8. Treatment means can thereby flow along the outside of the tool body 8*a* to the treatment point.

It is advantageous furthermore to provide the holding device 6 with a cam arrangement 116 for pressing the tool shank 8 out of the holding device 6. A cam arrangement 116 of this kind can be formed with a key drive and a wedge face 117 or curved face, which on movement of the actuating element 91 into its release position presses against the tool shank and displaces it in its removal direction. In the present configuration the wedge face 117 is formed by the rear flank of a preferably wedge-shaped spherical cap 118 in the inner sheath surface of the actuating sleeve 92*a*. The wedge face 117 is arranged such that in the ready position of the actuating sleeve 92*a* (shown in to FIG. 4) the tool shank 8 sits close to a deep point of the wedge face 117 or is at a short distance from it. The upper end of the tool shank 8 is preferably formed in a ball or wedge shape, so that it engages the wedge face 117 in the central area thereof. In the present configuration, a dome-shaped pressure element, or preferably a ball 119, is disposed in a recess 121 at the free end of the tool shank 8 and is secured therein against falling out. An essentially central point of application is thereby created for the wedge face 117 on the tool shank 8. If the ball 119 is held freely rotatably in the recess 121, the friction forces on ejection of the tool shank 8 are considerably reduced and handling is thereby made easier.

Since an actuating element 91 is assigned to the securing part for unlatching, the flanks 29*b* of the securing recess 28 can be formed to obtain greater axial securing forces. That is, they may be formed very steeply or also at right angles to the shaft axis 27*a* that no pressurization or 5 displacement of the securing part 29 from the securing recess 28 is possible.

In addition to the locking device 102, a further locking device 125 can be provided, preferably opposite it. In the present configuration the further locking device 125 is located at the back of the plug-in hole 27. A dome-shaped rounded securing lug 125*a* is provided on the end of a securing part 125*b*, and is displaceable between a securing position engaging in the securing recess 28 and a release position releasing it. The securing lug 125*a* is pre-tensioned by the force of a spring, here a pressure spring 126, into its securing position, so that the securing lug latches automatically on insertion of the tool shank 8. In this configuration, however, no direct mechanical connection is provided between the actuating element 91 and the securing part 125*b*. In the case of this locking device 125, therefore, the flanks 29*b* of the securing lug 125*a* or the securing recess 28 or spherical caps 31 are to be formed so flat that the securing lug 125*a* is displaced automatically from the securing recess 28 on displacement of the tool shank 8 in the plug-in hole 27. The locking device 125 is thus manually pressurizable.

It is possible within in the scope of the invention to form the holding device 6 only with the locking device 125, for example without the locking device 102 and also without the actuating element 91. In a configuration of this kind the securing lug 125*a* latches automatically on insertion of the tool shank 8, and the locking device 125 can be released automatically by exerting axial tension on the tool 7, the securing lug 125*a* being displaced from the securing recess 28. When the tool 7 has been removed, the securing lug 125*a* or the securing part 125*b* is positively prevented from falling into the plug-in hole 27.

In the present configuration, the securing lug 125*a* is formed on a cylindrical pin 125*c* which in turn is formed with a rear flange 125*d*. This flange is supported displaceably in a guide bushing 127 between its securing position and its release position transverse to the tool shank 8. A pressure spring 126 is provided in the guide bushing 127 for pre-tensioning the pin 125*c* against the tool shank 8. The spring 126 is supported at the rear on a locating face. The guide bushing 127 is inserted from the front into a corresponding threaded hole 128 and is screwed therein. A backwardly directed locating force 129 is provided at the front end of the guide bushing 127. The locating face 129 which forms a limit stop 131 which prevents the pin 125*c* also from falling out. This locking device 125 can also be formed corresponding to the locking device 102. The pin 125*c* has an axial through-duct 13*a* for the passage of the media line 13.

Figure 5:
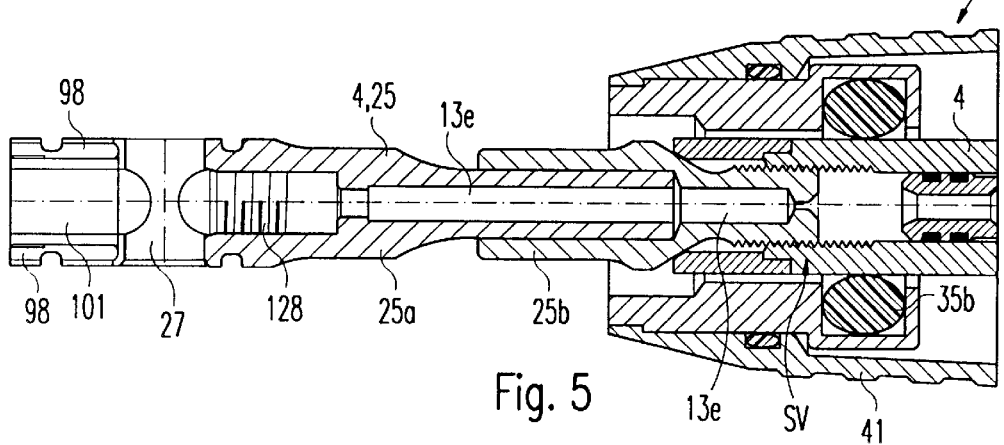
FIG. 5 shows the front end area of a treatment instrument in a modified configuration in axial section.
Figure 6:
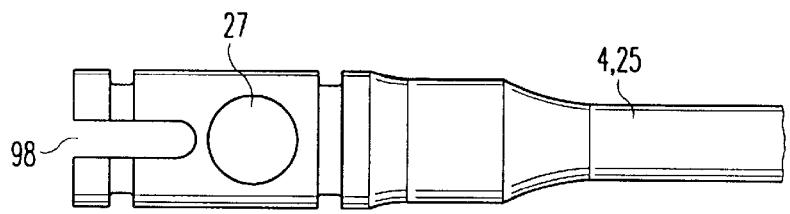
FIG. 6 shows a handpiece shank of the treatment instrument according to FIG. 5 in top view.

A further illustrated example of the invention is shown in FIG. 5. As shown, the handpiece shank 25, which protrudes beyond the gripping sleeve or the sleeve casing 41, is formed as a separate component, and is connected by a detachable connection, preferably a screw connection SV, coaxially to the preferably rod-shaped vibration part 4. The screw connection SV can be sunk in the front end area of the sleeve casing 41 and can be formed by a threaded pin at the rear end of the handpiece shank 25. In this case, the pin is screwed into a coaxial threaded hole in the vibration part 4. The screw connection SV can be provided within the elastically deformable bearing sleeve 35 as shown in FIG. 1 or inside the elastically deformable bearing ring 35*a* which centers the vibration part 4 elastically in a comparable manner. The bearing ring 35*a* sits in an annular groove of an inner sheath inserted in the front end area of the gripping sleeve or the sleeve casing 41. outside the sleeve casing 41 or the bearing sleeve 35 the handpiece shank 25 has a tool engaging element for fastening or undoing, e.g. a hexagon. In the present configuration, the handpiece shank 25 consists of two shank sections 25*a*, 25*b* arranged coaxially one behind another, which are plugged into one another for example in the form of a sleeve and fastened to one another, e.g. by gluing or by a press fit in the sleeve connection.

Figure 7:
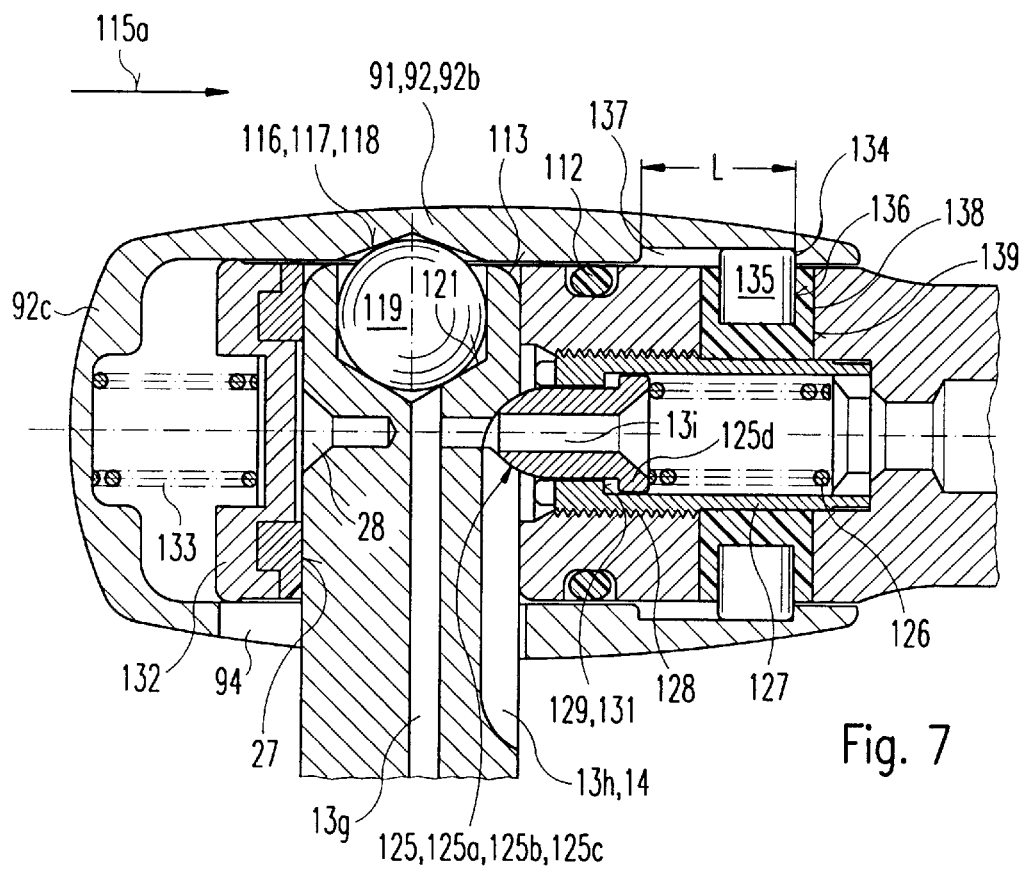
FIG. 7 shows the detail indicated by Y in FIG. 1, namely a holding device for a treatment tool in the front end area of the treatment instrument in axial section in a modified configuration.

To make it easier to release the tool shank 8, the holding device 6 can also be formed as shown in FIG. 7 with a device 116 for pressing the tool shank 8 out. An actuating element 91, likewise in the form of an actuating sleeve, can be used for this. The actuating element 91 may take the form of a sleeve 91*b* which is supported displaceably axially on the front end area of the handpiece shank 25. The actuating sleeve 92*b* can be closed at the front by an end wall 92*c*. A pressure spring 133 is disposed between the end wall 92*c* and a spring plate 132 for pre-tensioning the actuating sleeve 92*b* in its ready position. This is in contrast to the configuration according to FIG. 4, in which the front flank of the spherical cap 118 forms the wedge face 117. If the actuating sleeve 92*b* is displaced backwards according to the arrow 115*a* by axial pressure on its end wall 92*c*, the securing lug 125*c* is pressed out of the securing recess 28 and the tool shank 8 out of the plug-in hole 27 by the wedge face 117. To facilitate this movement, the plug-in recess 94 is lengthened forwards by the extent of the movement. In the ready position according to FIG. 7, the axial movement is limited by a limit stop 134 which can be formed by one or two stop pins 135 arranged opposing one another, which are supported in radial holes 136 of the handpiece shank 25 for radial displacement. The pins 135 are pre-tensioned by the force of a spring radially outwards. Each pin borders a longitudinal groove 137 in the inner sheath surface of the actuating sleeve 92*b*, the length L of which is designed to be larger by the extent of the axial movement than the related cross-sectional measurement of the stop pin 134, so that the actuating sleeve 92*b* can be displaced in its longitudinal position. The lateral surfaces of the longitudinal grooves 137 form, with the pins 135 bordering thereon, a rotational securing facility for the actuating sleeve 92*b*. In the present configuration, the stop pin 135 is taken up in each case in a pot-shaped bushing 138 of elastically deformable material such as rubber or synthetic material, which sits in a hole 139 of correspondingly large dimensions.

Figure 8:
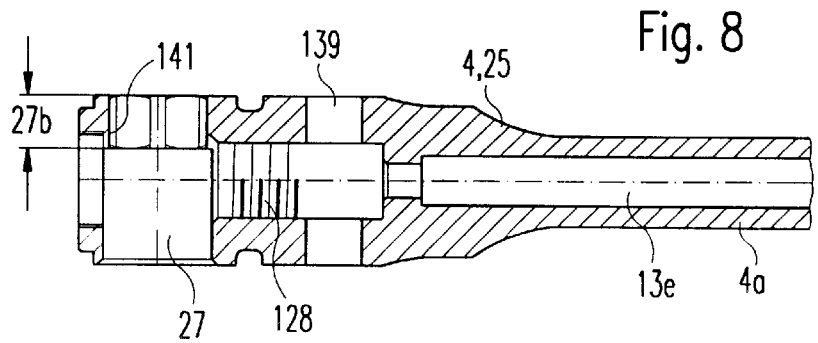
FIG. 8 shows the front end of a handpiece shank of the holding device according to FIG. 7 in a partly modified configuration in axial section.
Figure 9:
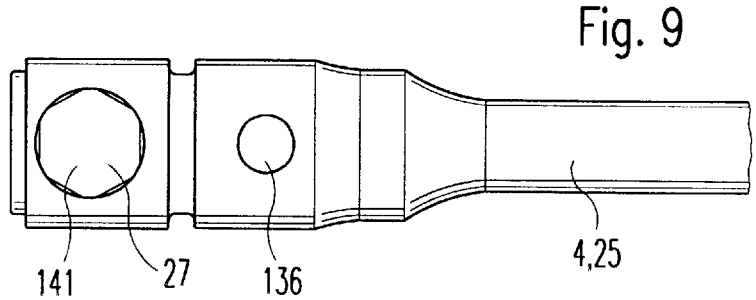
FIG. 9 shows the handpiece shank according to FIG. 8 in top view.

The rotary position setting device 114 can be formed in the shank 8 by a plug-in socket 141 instead of by spherical recesses 31. The socket and the tool shank 8 which is pluggable therein, each have a cross-sectional shape which is so out-of-round and so mutually matched that the tool shank 8 is pluggable therein in two or more positions twisted in relation to one another. If an out-of-round plug-in socket 141 exists, an annular groove of the appropriate cross-sectional shape can be arranged instead of spherical recesses 31. The cross-sectional shape of the plug-in socket 141 and of the tool shank 8 preferably has three or more, in particular six, regular corners. The cross-sectional shape can also be formed in the sense of a multi-tooth connection. The plug-in socket 141 does not have to extend over the entire length of the plug-in hole 27. It is sufficient for satisfactory functioning if only a section or the free end area of the tool shank 8 and a matching inner section or end area 27*b* of the plug-in hole 27 are formed as a plug-in socket 141, as shown in FIGS. 8 and 9. In this configuration, the securing recess 28 can be formed simply as an annular groove.

Figure 10:
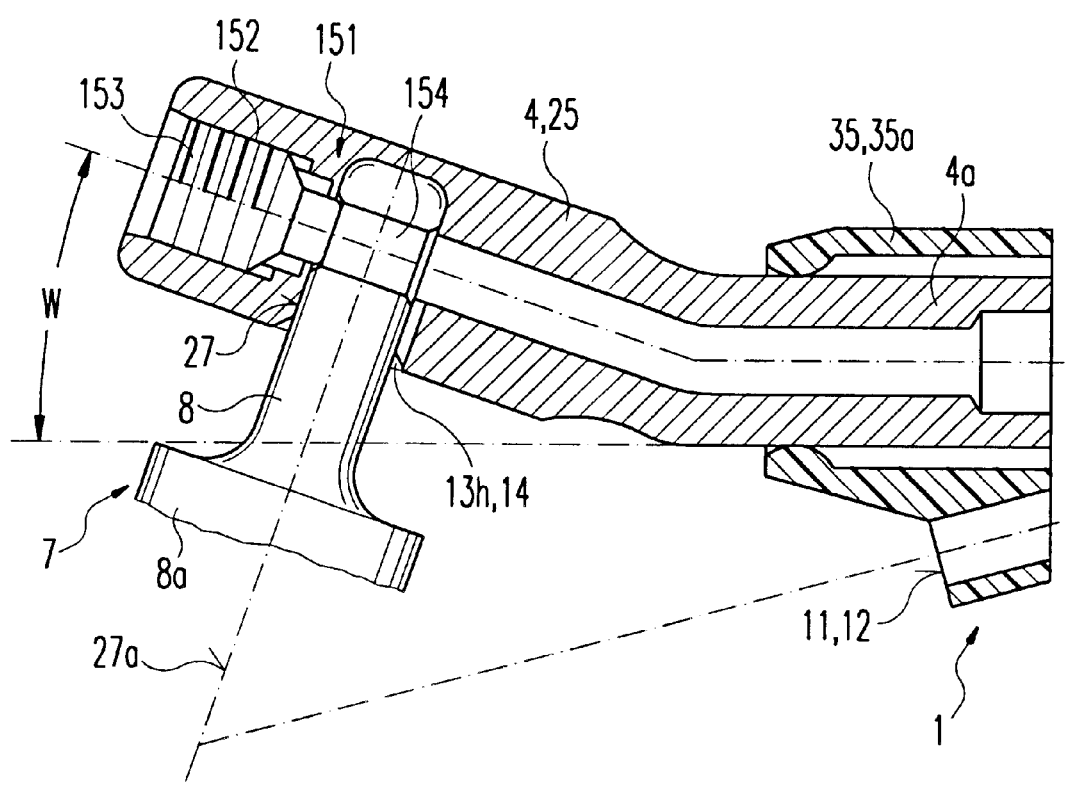
FIG. 10 shows the detail indicated by Y in FIG. 1, namely a holding device for a tool arranged in the front end area of the treatment instrument in axial section in a further modified configuration.

In the configuration according to FIG. 10, in which identical or comparable parts are provided with the same reference symbols, a screw connection or clamping joint 151 is provided instead of a locking device, with a securing screw 153 screwed preferably from the front into a threaded hole 152 of the handpiece shank 25. The screw 153 is screwable into an annular groove 154 or into one of several securing recesses distributed on the circumference of the tool shank 8 such that the screw 153 presses against the tool shank 8 to hold it in the plug-in hole 27. Alternatively the screw 153 projects partially into the recess with rotary movement play, to form a rotatable mounting or a rotary position setting device. With this configuration also, treatment fluid can be conveyed through a radial and/or axial duct in the tool shank 8 to at least one of the abrasive working surfaces of the tool 7 or through a longitudinal groove 13*h* disposed on the tool shank 8 or in the wall of the plug-in hole 27, thereby providing an outlet for the treatment fluid on the outside of the tool 7.

Figure 12:
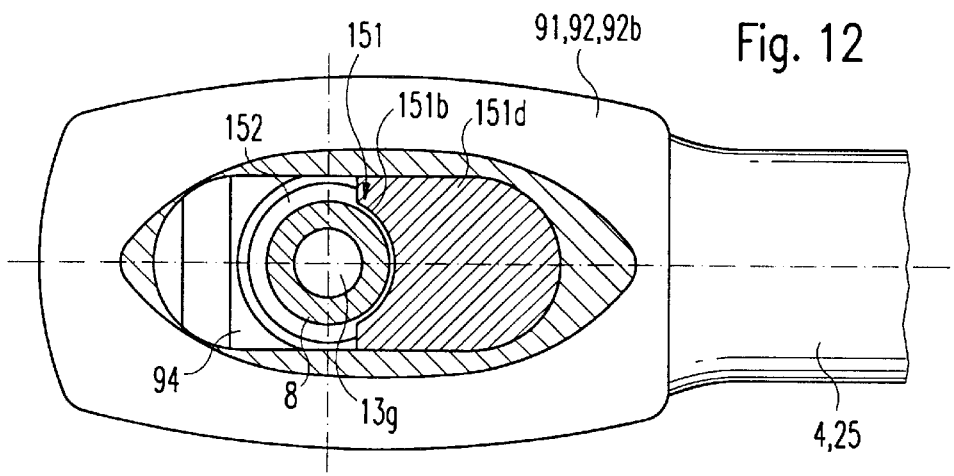
FIG. 12 shows the section XII—XII in FIG. 11.
Figure 11:
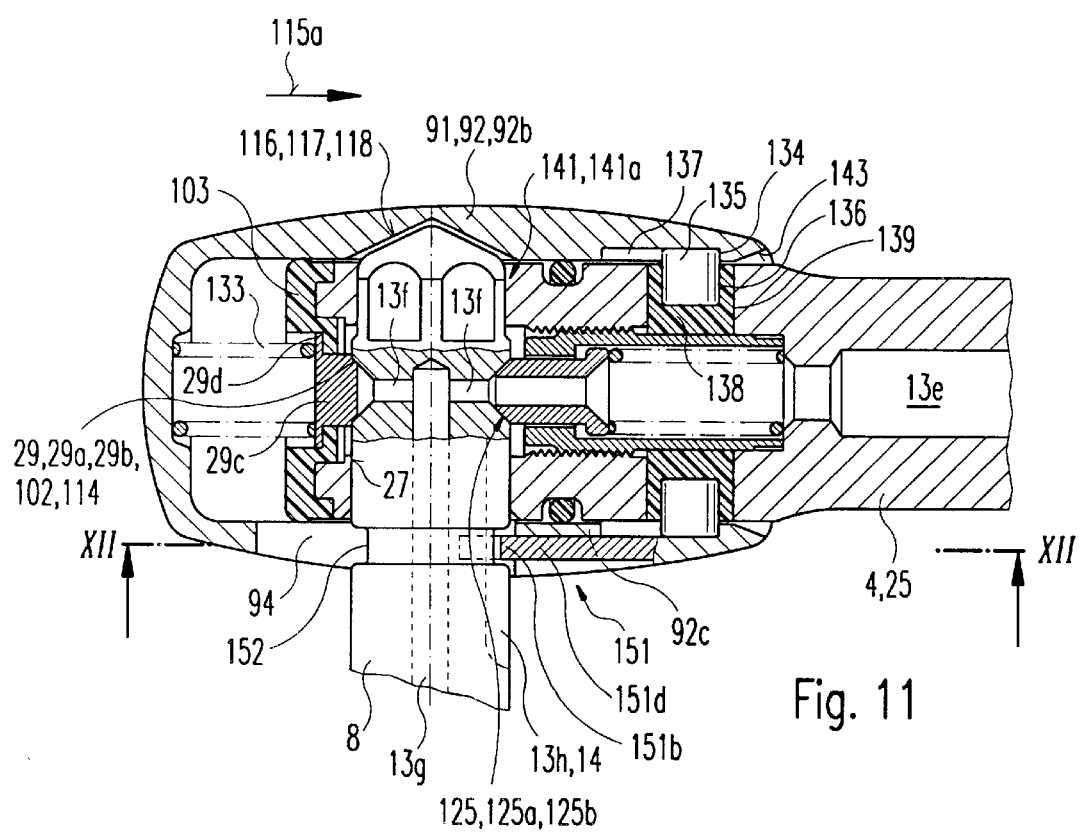
FIG. 11 shows a view corresponding to FIG. 10 in a further modification configuration.

FIGS. 11 and 12 show several practical examples which can be arranged in combination or individually. In FIGS. 11 and 12 identical or comparable parts are provided with the same reference symbols as in the preceding Figs.

An actuating sleeve 92*b* corresponding to the sleeve shown in FIG. 7 is displaceable rearwardly in the direction of the arrow 115*a* (FIG. 11) to release the tool shank 8 as previously described. A previously described plug-in socket 141 is also provided between the tool shank 8 and the handpiece shank 25.

To hold the tool shank 8 axially, a securing lug 29*b* can be provided instead of or in addition to the locking device 125. The lug 29*b* engages or is pre-tensioned by a spring 133 in a spherical recesses 31 or annular groove of the tool shank 8. However, the lug 29*b* is removable or displaceable from the spherical recess 31 or the annular groove independently of any movement of the actuating element 91. Starting out from the configuration shown in FIG. 7, the securing lug 29*b* is moved for this purpose by the spring 133 into its securing position, it being possible to form the securing lug 29*b* as a single piece on the spring plate 132 or mount it as a separate component whereby it is acted upon by the pressure spring 133. In the present configuration, the securing lug 29*b* is formed on a prismatic or cylindrical pin 29*c*, which is inserted from the front into a hole of the spring plate 132 and has at its end opposite the lug a flange 29*d*, which sits close to the side of the spring plate 132 opposite the plug-in hole 27, preferably close to the stepped surface of a stepped hole. Both in the configuration according to FIG. 4 and in the configuration according to FIG. 11, the securing lug 29*b*, instead of having a convexly rounded shape, may have inclined surfaces or a truncated conical surface on a lug stub which enters only partially into in the spherical recess 31 or annular groove.

It is also advantageous to form the rear edge of the actuating sleeve 92*b* in the shape of a rearwardly diverging insertion rounding or bevel 143 in alignment with the longitudinal groove or grooves 137. This facilitates assembly and dismantling of the actuating sleeve 92*b*. When pushing the actuating sleeve 92*b* on from the front, the insertion bevel 143 ensures automatic spring deflection of the related stop pin 135, which latches behind the limit stop 134 automatically into the related longitudinal groove 137. As is clearly seen in FIG. 11, the insertion bevel 143 ends above the related bushing 138. For dismantling the actuating sleeve 92*b* using a pointed tool such as a screwdriver, it is thereby possible to insert the tool into the wedge of the insertion bevel 143 and push the bushing 138 with the related stop pin 135 sufficiently to allow the actuating sleeve 92*b* to be removed.

In the configuration according to FIGS. 11 and 12 there is also provided locking device 151 for securing the tool shank 8 in its position within the holding device 6. The locking device 151 has a securing lug 151*b* on a locking or securing part 151*a*, which is connected fixedly to the actuating slide element 92, here the actuating sleeve 92*b*. The securing lug 151*b* is movable with the actuating slide 92 and forms a movement unit. This securing lug 151*b* can be formed by a transverse web on the actuating slide 92, which web protrudes in the ready position into the plug-in hole 27 or into its projection or extends secantially to it and engages in a locking recess 152 or annular groove in the tool shank 8. The securing lug 151*b*, as seen along the plug-in hole 27, can be formed concavely in adaptation to the cross-sectional shape of the annular groove base (e.g. be rounded), so that it can grip around the tool shank 8 in the shape of a sickle. Opposite the securing lug 151*b*, the plug-in recess 94 for the tool shank 8 is lengthened so that the actuating slide 92 is displaceable into its release position (not shown), here displaced to the right, in which release position the securing lug 151*b* is moved out of the securing recess 152.

The locking device 151 can be arranged preferably on the tool side of the handpiece shank instead of, or in addition to, the locking device 102 and/or 125. The device 116 for pressing the tool shank 8 out can also be provided. In this case, on displacement of the actuating slide 92 into its release position, the securing lug 151*b* is pushed directly out of the securing recess 152 and the tool shank 8 is pushed out at the same time by the wedge face 117.

In the present configuration, the securing lug 151*b* is formed by a flat disc, which is inserted into a recess 154 laterally adjacent to the plug-in recess 94 and fastened, e.g. by gluing or welding. The recess 154 can be made less deep than the thickness of the circumferential wall of the actuating sleeve 92*a*, so that a wall section 92*c* remains, which the disc can sit close to.

The handpiece shank 25 and the parts of the holding device 6 can consist of corrosion-resistant metal and/or synthetic material. In the previously described practical examples, the parts shown with parallel hatching consist of metal and the parts with cross-hatching of synthetic material.

The configurations according to the invention also yield an advantageous tool configuration in the area of the tool shank 8. It should be emphasized in this regard that the tool shank 8 has securing recesses which are used for axial securing and rotational securing. The spherical recesses 31 and/or the plug-in pin 141*a*, which are arranged preferably at the free end, have the tool shank 8 on the tool shank 8 of an out-of-round configuration, e.g. a hexagonal cross-section, so that they can be used for rotational securing. In a regular arrangement of this polygon or the spherical recesses 31, a rotary position setting device for the tool 7 can also be realized, which facilitates the arrangement positioning of the tool 7 in different rotary positions. If a polygonal plug-in pin 141*a* is present, an annular groove can be provided in the tool shank 8 instead of several spherical recesses 131. In the case of a tool 5 which does not need to be set in different rotary positions, the locking recess 152 can be formed by a lateral recess. An annular recess is particularly suitable for different rotary positions. In the case where a plug-in pin 141*a* with out-of-round cross-section is provided as a rotational securing facility, the securing recess 152 can be provided in addition to or instead of the spherical recesses 31 or an annular groove. For supplying the treatment or cooling fluid, the inner duct section 13*g*, which emerges inside or above one or several working surfaces of the tool 5, and/or the outer longitudinal groove 13*h*, can be provided. The duct section 13*g* is connected to the supply line extending axially in the handpiece shank. One or two exit openings 13*i* formed by branches are shown by way of example in FIG. 1.

Figure 13:
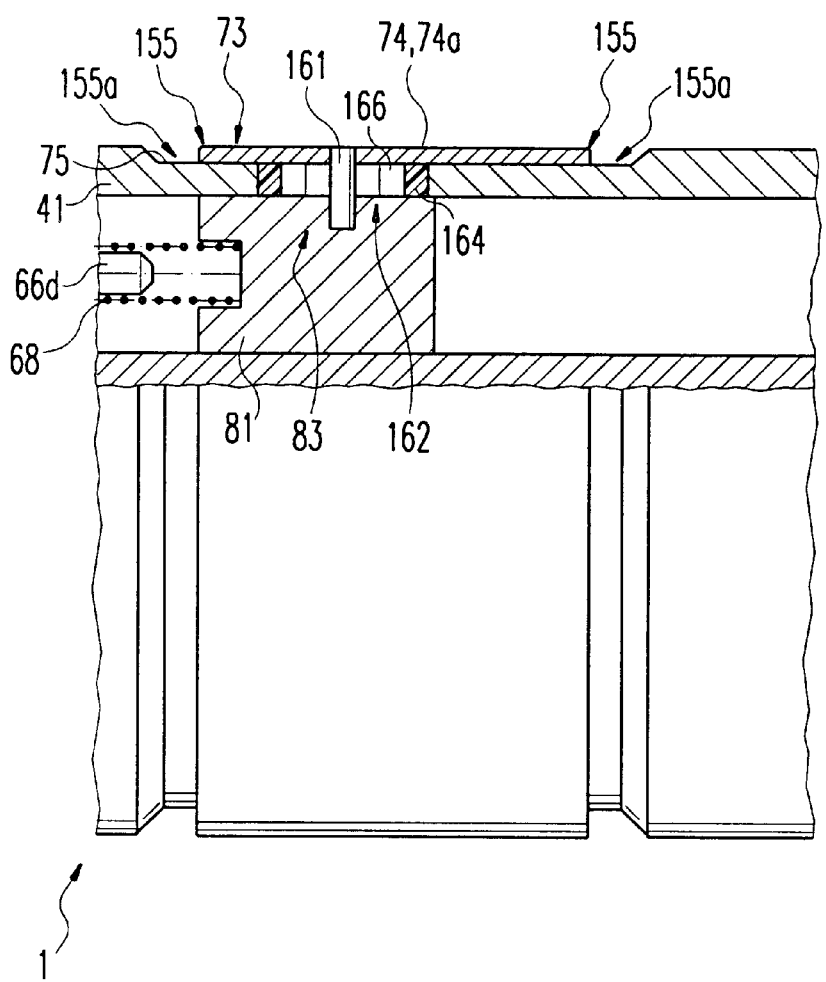
FIG. 13 shows a longitudinal section of a treatment instrument according to the invention in modified configuration in axial section.

Different tools 7 for performing different treatments can be utilized with the treatment instrument 1 as needed or desired. These tools 7 can be of e.g. different shapes and/or mass and/or nature of the abrasive working surface, e.g. rough, medium, fine and/or can be tools 7 which are equipped or not for the supply of a treatment medium, e.g. cooling fluid. Different output requirements can exist for such different tools in order to attain an optimum function or working capacity. In regard to tools 7 of different mass, such different requirements can be due to the fact that the mass vibration at an output setting of a specific magnitude is particularly advantageous, e.g. taking account of vibration resonances. In regard to tools 7 which have a different nature of their abrasive working surfaces, such as e.g. rough, medium, or fine, an output setting of a specific magnitude to improve performance is likewise advantageous. It is also to be taken into consideration with regard to this criterion that the working surfaces can become clogged with chips and a specific output setting is also therefore advantageous. An output setting of a specific magnitude is also advantageous in the case of tools 7 which operate with a cooling fluid. As shown in FIG. 13, markings 155 are advantageously arranged on the treatment instrument 1 for the setting element 74 so that by setting the element 74 in the direction of a certain marking, an output is set which is advantageous for an assigned tool 7. Color coded or other markings, e.g. symbols, may be used; and each of which may have a related index 155*a* the setting path on the treatment instrument to indicate a set position. In the present configuration, one or more markings 155 and one or more related indices 155*a* can be arranged on the setting element 74 and on the gripping sleeve. Alternatively, the sleeve casing 41, as shown in simplified form, e.g. in the form of a scale, the markings 155 are arranged on one part and at least one index 155*a* are arranged on the other part. A corresponding marking can be arranged in each case on the tool 7, e.g. on the tool shank 8 close to the tool head. Different colors are particularly suitable for distinguishing one pair of markings 155, 155*a* from another pair of markings 155, 155*a*, with markings which correspond to one another preferably having the same color.

Figure 14:
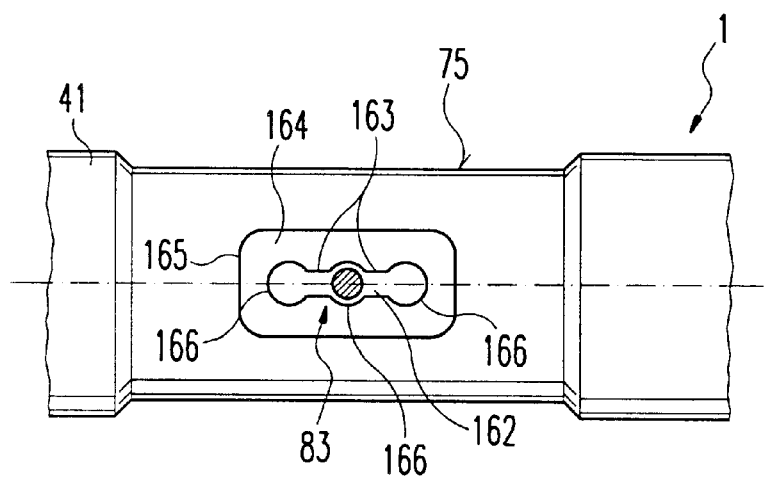
FIG. 14 shows the longitudinal section according to FIG. 13 in top view.

In the illustrated example shown in FIGS. 13 and 14, in which identical or comparable parts are provided with the same reference symbols, as in the previous drawings, the setting device 73 has a setting element 74 which is preferably also in the form of a setting sleeve 74a. The setting device 73 is axially displaceable in the groove 75, which is designed to be correspondingly longer; and the setting device 73 is moveable, either steplessly or in increments, and is fixable in each set position by the fixing device 83. In this configuration, the adjusting element 81 is connected by a radial connection pin 161 rigidly to the setting element 74. The connection pin 161 extends into a setting groove 162 running longitudinally in the sleeve casing and the longitudinally aligned groove walls 163 clamp the connection pin 161 so strongly that the connection pin can be moved axially only by application of a manual force outlay; otherwise the pin is fixed against unintentional displacement by the clamping effect of the groove walls 163. For this purpose the setting groove 162 can be formed in an insert part 164 of elastically deformable material, e.g. synthetic material, which sits in a corresponding recess 165 in the sleeve casing 41. If certain setting points are to be realized, latching recesses 166 can be arranged in one or both groove walls 163, in which recesses the connection pin 161 can latch. In the present configuration, three latching points are arranged axially behind one another. To clarify this, the longitudinal section of the treatment instrument 1 shown in FIG. 14 is shown without the setting sleeve 74a. The markings 155 155a can be arranged in this configuration on the front edge or rear edge of the setting element 74 and the sheath surface of the sleeve casing 41 located adjacent to it.

What is claimed is:

1. Medical or dental treatment instrument for chip removing treatment of body tissue or a substitute material with an abrasive tool, said instrument comprising:

a handpiece:

a vibration part for supporting a tool and located in a front end area of said handpiece;

a vibration generator arranged in the handpiece, said vibration generator being drivable by compressed air;

a flexible compressed air supply line arranged to connect said vibration generator to a power supply; and a control device constructed and arranged to increase and decrease the output of said vibration part, said control device being formed by a control valve which includes a valve slide which controls the size of a valve opening in said compressed air supply line, said valve slide being moveable and arranged to be acted upon by pressure available at the vibration generator against the force of a spring; said valve slide having a control edge which is positioned to control the size of said valve opening.

2. Medical or dental instrument as claimed in claim 1, and further including:

a setting device which includes a manually adjustable setting element, said setting element being moveable on said handpiece against said spring to change its force.

3. Medical or dental treatment instrument as claimed in claim 2, wherein at least one of the setting device and the control valve is disposed in the handpiece.

4. Medical or dental treatment instrument as claimed in claim 3, wherein:

the setting element is disposed in the rear end area of the handpiece.

5. Medical or dental treatment instrument as claimed in claim 2, wherein:

the setting element is arranged on a sheath surface of the handpiece and is adjustable in a circumferential direction of said handle.

6. Medical or dental treatment instrument as claimed in claim 5, wherein:

said setting element is formed by a sleeve.

7. Medical or dental instrument as claimed in claim 2, wherein:

the setting device includes an adjusting element which is supported moveably in the handpiece to move against an end of said spring, said adjusting element being in contact with an oblique face of a segment which is moved by said setting element.

8. Medical or dental treatment instrument as claimed in claim 2, wherein:

the setting device includes an adjusting element arranged to move axially in the handpiece against one end of said spring, said adjusting element being in contact with the setting element by a mechanism which is constructed and arranged to move in an axial direction corresponding to the direction of movement of the adjusting element.

9. Medical or dental treatment instrument as claimed in claim 2 which protrudes radially inwards from the setting element through a slot in the handpiece, said web having an oblique or a curved face on one side thereof.

10. Medical or dental treatment instrument as claimed in claim 2, wherein:

the setting element is connected to move an adjusting element against one end of said spring.

11. Medical or dental treatment instrument as claimed in claim 2 and further including:

a manually pressurizable fixing or locking device which is operable to secure the setting device in a set position.

12. Medical or dental treatment instrument as claimed in claim 2, wherein:

the setting element is moveable along an adjusting path on a part adjacent thereto and wherein there is provided marking on the setting element and on said part adjacent thereto which provides indications of the amount of adjustment of the setting part and the location of latching points.

13. An instrument as claimed in claim 12, wherein the marking includes different symbols or colors.

14. In combination with a treatment instrument as claimed in claim 12, a plurality of different tools having different shapes, sizes, firmnesses and tissue removal capacities.

15. An instrument combination as claimed in claim 14, wherein said different tools have different markings and marking positions on the respective tool shanks and different associated latching points on respective adjusting paths according to particular operating characteristics of the respective tools.

16. Medical or dental instrument as claimed in claim 1, wherein said valve slide is mounted to be axially moveable.

17. Medical or dental treatment instrument for chip-removing treatment of body tissue or a substitute material with an abrasive tool, said instrument comprising:

a handpiece;

a vibration part for supporting the tool;

said vibration part being supported in a front end area of the handpiece;

a vibration generator connected and arranged to cause the vibration part to vibrate, the vibration generator being drivable or excitable by compressed air;

a supply line extending through the rear end area of the handpiece and connected to said vibration generator for supplying compressed air thereto; and a pressure regulator provided in the supply line within said handpiece, said pressure regulator being configured to maintain an essentially constant working pressure at the vibration generator even in the presence of operating pressures in said supply line of differing levels.

18. Medical or dental treatment instrument as claimed in claim 17, further including:

said pressure regulator including valve slide, said valve slide being displaceable in response to a working pressure against the force of a spring, said valve slide being arranged to move over a valve opening so as to decrease the size of the valve opening in response to a greater operating pressure and to increase the size of said valve opening in response to a smaller operating pressure.

19. Medical or dental treatment instrument as claimed in claim 1 or 18, wherein there are provided both a control device to increase and decrease the output of said vibration part and a the pressure regulator to maintain an essentially constant working pressure at the vibration generator.

20. Medical or dental treatment instrument as claimed in claim 19, wherein:

the control device is arranged such that it acts or on the valve slide via the spring.

21. Medical or dental treatment instrument a claimed in claim 20, wherein:

the control device is constructed and arranged to move against one end of said spring to vary the force of the spring.

22. Medical or dental treatment instrument as claimed in claim 17, wherein the pressure regulating valve is disposed in the handpiece.

23. Medical or dental instrument for chip removing treatment of body tissue or substitute material with an abrasive tool, said instrument comprising:

a handpiece having a grip sleeve;

a vibration part located in a front end area of the grip sleeve, said vibration part supporting a tool;

a pneumatically operated vibration generator arranged to cause the vibration part to vibrate;

a flexible supply line which extends from a supply device said handpiece being connected at its rear end area to said flexible supply line;

an additional inner casing within said grip sleeve and surrounding said vibration generator, the walls of said additional inner casing being at a radial distance from the vibration generator and from sad grip sleeve, said inner casing being formed as a sleeve;

said vibration generator being driveable pneumatically and having a hollow rod-shaped vibration part extending parallel to a longitudinal axis of said handpiece, said hollow vibration part being connected to receive compressed air from said supply line;

said vibration part having radial compressed air exit holes;

a vibrating sleeve surrounding and spaced from said vibration part in the area of said radial compressed air exit holes;

an outer casing positioned over said inner casing such that between the inner casing and said outer casing a first radial distance is provided, and such that between the inner casing and the vibrating sleeve a further radial distance is provided; and said inner casing being formed with an air outlet.

24. Medical or dental instrument for chip removing treatment of body tissue or substitute material with an abrasive tool, said instrument comprising:

a handpiece having a grip sleeve;

a vibration part located in a front end area of the grip sleeve, said vibration part supporting a tool;

a pneumatically operated vibration generator arranged to cause the vibration part to vibrate;

a flexible supply line which extends from a supply device;

said handpiece being connected at its rear end area to said flexible supply line;

an additional inner casing within said grip sleeve and surrounding said vibration generator, the walls of said additional inner casing being at a radial distance from the vibration generator and from sad grip sleeve, said inner casing being formed as a sleeve; and axially spaced bearing rings of elastically deformable material disposed between the rear and front end areas of said sleeve and said vibration part, a front one of said bearing rings being air-permeable.

25. Medical or dental treatment instrument as claimed in claim 24, wherein at least one of said bearing rings consists of a material chosen from the group consisting of rubber, synthetic material and felt.

26. Medical or dental treatment instrument as claimed in claim 24, wherein the inner casing is connected at its rear end to a bearing ring in the form of a sleeve.

27. Medical or dental treatment instrument for chip removing treatment of body tissue or a substitute material with an abrasive tool, said instrument comprising:

a handpiece having a grip sleeve;

a vibration part mounted in a front end area of said grip sleeve for supporting a tool;

a vibration generator arranged to vibrate the vibration part;

said vibration part protruding beyond the grip sleeve in the form of a handpiece shank with such tool being laterally spaced apart from the handpiece shank said handpiece connected at its rear end area to a flexible supply line, which extends from a supply device; and an optical fiber extending through said handpiece and through a bearing ring which extends forwardly from the handpiece, said optical fiber being accommodated in a duct in the vibration part, said vibration part being mounted eccentrically in the grip sleeve towards the side opposite the tool, and said bearing ring being eccentric.

28. Medical or dental treatment instrument as claimed in claim 27, wherein the bearing ring protrudes beyond the front end of the handpiece in the form of a sleeve.

29. Medical or dental treatment instrument as claimed in claim 27, wherein the bearing ring is fixed to extend axially from a front cover of a gripping sleeve portion of said housing.

* * * * *